(12) United States Patent
Riad et al.

(10) Patent No.: US 11,291,857 B2
(45) Date of Patent: Apr. 5, 2022

(54) METHODS FOR TREATMENT PLANNING

(71) Applicant: ELEKTA LTD., Crawley (GB)

(72) Inventors: Stella Riad, Sundbyberg (SE); Håkan Nordström, Sollentuna (SE); Emil Norell, Stockholm (SE)

(73) Assignee: ELEKTA LTD., Crawley (GB)

( * ) Notice: Subject to any disclaimer, the term of this patent is extended or adjusted under 35 U.S.C. 154(b) by 94 days.

(21) Appl. No.: 16/786,434

(22) Filed: Feb. 10, 2020

(65) Prior Publication Data

US 2020/0282236 A1 Sep. 10, 2020

Related U.S. Application Data

(60) Provisional application No. 62/815,166, filed on Mar. 7, 2019.

(51) Int. Cl.
*A61N 5/10* (2006.01)

(52) U.S. Cl.
CPC ......... *A61N 5/1031* (2013.01); *A61N 5/1065* (2013.01); *A61N 5/1071* (2013.01)

(58) Field of Classification Search
CPC .......... A61N 5/00; A61N 5/10; A61N 5/1031; A61N 5/1071; A61N 5/1065; A61N 5/1084
See application file for complete search history.

(56) References Cited

U.S. PATENT DOCUMENTS 6,201,988 B1    3/2001  Bourland et al.
9,358,404 B2 *  6/2016  Danielsson ............ A61N 5/103

OTHER PUBLICATIONS

Ghobadi et al., "Automated treatment planning for a dedicated mult-source intracranial radiosurgery treatment unit using projected gradient and grassfire algorithms," Med. Phys., vol. 39, No. 6, 2012, pp. 3134-3141 (Abstract only).

* cited by examiner

*Primary Examiner* — Jurie Yun
(74) *Attorney, Agent, or Firm* — Birch, Stewart, Kolasch & Birch, LLP

(57) ABSTRACT

In the field of radiotherapy, methods for dose or treatment planning for a radiation therapy system having a collimator, includes determining shots to be delivered during said treatment, each shot being associated with an isocenter and being modelled by a spatial dose volume distribution of radiation, the shape of said spatial distribution depending on the specific collimator setting and said selected dose level, including selecting isocenter positions within a target in a predetermined angle range; evaluating each isocenter based on predetermined conditions; selecting at least a specific collimator and sector setting for each isocenter based on the evaluation; calculating a dose for the selected isocenters; repeating the steps until at least one stopping criteria has been reached, wherein a final set of isocenters are provided; and using the final set of isocenters in treatment planning.

20 Claims, 6 Drawing Sheets

METHODS FOR TREATMENT PLANNING

CROSS REFERENCE TO RELATED APPLICATIONS

This non-provisional application claims the benefit under 35 U.S.C. § 119(e) to U.S. Provisional Application No. 62/815,166, filed on Mar. 7, 2019, which is hereby expressly incorporated by reference into the present application.

FIELD OF THE INVENTION

The present invention relates to the field of radiotherapy or radiation therapy. In particular, the invention relates to methods and systems for planning and optimizing treatment sessions of a patient in radiotherapy or radiation therapy systems such as the Leksell Gamma Knife® Icon™.

BACKGROUND OF THE INVENTION

The development of surgical techniques has made great progress over the years. For instance, patients in need of brain surgery may instead have non-invasive surgery which drastically reduces the trauma to the patients.

Systems for non-invasive surgery include the Leksell Gamma Knife® Icon™ and the Leksell Gamma Knife® Perfexion, which provide such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which, by itself, is insufficient to damage intervening tissue. However, tissue destruction occurs where the radiation beams from a plurality of radiation sources intersect or converge, causing the radiation to reach tissue-destructive levels. The point of convergence is hereinafter referred to as the "focus point".

Treatment plan optimization in radiotherapy, including for example gamma knife radiosurgery, aims at delivering sufficiently high dose to the target volume within the patient (e.g. in treatment of tumours) at the same time as the dose delivered to adjacent normal tissue is minimized. In treatment plan optimization, at least three competing factors have to be considered: delivering a sufficiently high dose to the target volume, sparing the surrounding normal or healthy tissue and keeping the treatment time as short as possible.

The treatment plan optimization is a process including optimizing the relative isocenter locations (i.e. position of the focus point), and collimator configuration. In, for example, the Leksell Gamma Knife® Icon™ and the Leksell Gamma Knife® Perfexion the treatment plan optimization may include optimizing the number of shots being used, the collimator configuration of each shot, the shot times, and the position of the shot.

Clearly, the irregularity and size of a target volume greatly influence the number of shots needed and the size of the shots being used to optimize the treatment. Normally, the process includes obtaining a three-dimensional representation of the target (e.g. by non-invasive image capturing by X-ray) for the radiation therapy and filling the target with spheres representing the shots without extending area strongly dosed by radiation greatly outside the target and without limited overlap between shots). It has been shown that in order to preserve dose homogeneity and in a multi-shot plan, shots should not overlap with each other in a too great extent. Further, shots protruding outside the target may result in excessive dose to surrounding normal tissues. This requires, for targets of identical volume yet different shapes, use of small shots for complicated contours (i.e. for targets having an irregular shape) and larger shots for regular shapes. In U.S. Pat. No. 6,201,988 to Bourland et al, such an optimization procedure is disclosed. Medial axis transformation (so called skeletonization) is used to characterize the target shape and to determine the shot parameters (i.e. position, collimator size and weight). According to U.S. Pat. No. 6,201,988, only skeleton points are considered for potential shot positions and the corresponding shot size is provided by the skeletonization. The shots are represented by spheres and are modeled as discs in filling process. The endpoints of the skeleton are used as start-points in the filling process. However, the treatment planning optimization shown in U.S. Pat. No. 6,201,988 may provide treatment plans having a non-optimal distribution of shot sizes, for example, an unnecessary large amount of small shot sizes may be included leading to a large number of shots being used.

Another approach that have been used is the well-known grassfire algorithm with a sphere packing routine as described in Ghobadi K, Ghaffari H, Aleman D, Jaffray D and Ruschin M, Automated treatment planning for a dedicated multi-source intracranial radiosurgery treatment unit using projected gradient and grassfire algorithms, Med. Phys. (2012) 39 3134-41.

A further approach and improved procedures for target volume filling is described in U.S. Pat. No. 9,358,404 and in pending applications by the same applicant. In U.S. Pat. No. 9,358,404 an iterative approach based on that shots are selected in decreasing volume order for the dose planning. These methods are geometry based.

Hence, there still remains a need for improved and more computational efficient methods for planning and optimizing the treatment.

SUMMARY OF THE INVENTION

An object of the present invention is to provide more efficient dose planning methods, modules and systems for planning the treatment and for optimizing the treatment planning.

A further object of the present invention is to provide more efficient methods, module, and systems for filling a target volume with shots during a treatment planning procedure.

These and other objects are fulfilled by the present invention as defined by the independent claims. Preferred embodiments are defined by the dependent claims.

The term "target" or "target volume" refers to a representation of a target of a patient to be treated during radiotherapy. The target may be a tumour to be treated with radiotherapy. Typically, the representation of the target is obtained by, for example, non-invasive image capturing using X-ray or nuclear magnetic resonance.

The term "shot" refers to a delivery of radiation to a predetermined position within a target volume having a predetermined level of radiation and a spatial distribution. The shot is delivered during a predetermined period of time ("beam-on" time) via at least one sector of the collimator of the therapy system using one of the states of the sector. A "composite shot" refers to the delivery of radiation to a focus point using different collimator sizes for different sectors.

The term "beam-on time" refers to the predetermined period of time during which a shot is delivered to the target volume.

The term "voxel" is used in the context of this application and refers to volume elements on a grid, which may be anisotropic in a three-dimensional space.

The term "structure" refers to a volume, which can be defined in voxels, such as a target or organ at risk ("OAR").

The present invention is for example used in connection with treatment planning of treatment provided by means of a radiation therapy system having a collimator body provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having three different states (4 mm, 8 mm, and 16 mm) or four if "beam-off" is included. The sectors can be adjusted individually, i.e. different states can be selected for each sector, to change the spatial distribution of the radiation about the focus point.

The present invention may also be used in connection with treatment planning of treatment provided by means of a radiation therapy system having a rotatable collimator body provided with several groups or sets of collimator passages, each set being designed to provide a radiation beam of a respective specified cross-section toward a fixed focus point. The collimator body is configured to rotate around the z-axis (with reference to the figures) or around an axis along a translational direction of the patient.

On a general level, the present invention is based on column generation and use of inverse planning methods with convex problems, described in pending patent applications by the same applicant.

Generally, the optimization problem can be formulated as $$\min_{t} f(d, t)$$
$$\text{s.t. } d = \Phi t$$
$$d \in D, t \geq 0$$

Where $f(d,t)$ $\mathbb{R}^{N_j \times F} \to \mathbb{R}$ is a penalty based cost function that evaluates a distribution of dose d in the $N_j$ voxels along with the times t spent in different degrees of freedom ("DoFs") and $\phi$ is the dose rate matrix. The function $f$ is designed so that the optimal plan is found by minimizing the problem. The dose $d(t)$: $\mathbb{R}^{N_j \times F} \to \mathbb{R}$ is in turn a function of all beam delivery times in t, the times must satisfy $t \geq 0$. Let D be the feasible region for the dose that fulfill predetermined criteria on the dose to structures, e.g. to the OARs. The general formulation of the sector duration optimization formulation then becomes as above.

According to embodiments, a predetermined large number of isocenter positions, N, are determined prior to the initialization of the column generation algorithm and their corresponding contributions to the dose rate matrix are computed. For each isocenter, there are 24 corresponding columns in the dose rate matrix (in the primal formulation of the problem). That is, three states and eight sectors for each isocenter. At every iteration k, the optimization problem can be written, after the introduction of slack variables, on the form.

$$\min c^T \chi \quad (1)$$
$$\text{s.t. } A_k \chi = b,$$
$$\chi \geq 0,$$

Where X consists of $t_{csi}$ that are the times for each isocenter position i, sector s and collimator c respectively, and the slack variables, $A_k$ is the matrix of coefficients at iteration k, i.e. containing the contributions from the k chosen DOFs to the structures considered in the problem in the columns. The cost function is $c^T X$.

In the inverse planner, the cost function is a weighted sum. The weight settings for the isocenter generation procedure can either be chosen generic, i.e. using some weight setting that generally produces clinically acceptable plans with respect to conformality, or specific to the weight settings chosen based on the user's specific preferences for the problem. In order to determine which isocenter that can give the largest improvement to the objective function value, and thus, which isocenter to add to the master problem in (1), the reduced cost for the isocenters not yet included in the master problem are computed.

Note that adding isocenters implies that elements are added to the solution vector. The reduced cost for the degree of freedom is defined as $$r_m = c_m - \sum_{l=1}^{N_j} \lambda_l \phi_{lm}, \quad (2)$$

Where $c_m$ is the coefficient of the objective corresponding to the candidate variable $\lambda_l$ are the Lagrange multipliers from the solution of the master problem, $N_j$ are the number of voxels and $\phi_{lm}$ is an element in the dose rate kernel corresponding to the candidate DOF. In principle, the column with the largest negative reduced cost should be added to the problem. However, since there are 24 columns corresponding to each isocenter, the isocenter is chosen based on a heuristic computed from the reduced costs, such as the sum, a weighted sum or the maximum values. The isocenter determination is initiated by choosing a first isocenter according to some criteria, for example the isocenter with the largest negative value of $r_m$, assuming the Lagrange multipliers to be equal to one (1) or assume that the first isocenter position is in the center of the target. The iteration proceeds until at least one predetermined stopping criteria is met, e.g. when the heuristic for the best isocenter is below a limit $r_{stop}$ or the number of iterations, k, exceeds a predetermined limit, $n_{max}$. The steps in the iteration are the following:

1. Solve the master problem for iteration k to update the Lagrangian multipliers $\lambda$.
2. For each column corresponding to the candidate isocenter positions compute the reduced cost.
3. Add the isocenter with smallest value of the heuristic to the dose rate matrix in the optimization problem.
4. Repeat step 1-3 until the stopping criteria has been reached.

According to embodiments, the method is used in treatment planning for radiotherapy or radiation therapy systems such as the Leksell Gamma Knife®. The collimator body is provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

In further embodiments of the present invention, the collimator body is rotatable around the z-axis or around an axis along the translational direction of the patient. According to embodiments, there is provided a method for dose planning for a radiation therapy system, a radiation therapy unit, wherein a spatial dose distribution surrounding the focus point can be changed by adjusting collimator settings, the collimator having a plurality of collimator passage inlets directing radiation emanating from radioactive sources of a source carrier arrangement of the therapy system to a focus point, it is obtained a target volume of a region of a patient to be treated during a treatment of a patient in a radiation therapy unit and a dose level for the planned treatment is selected. Then, shots to be delivered during the treatment is determined, each shot being associated with an isocenter and being modelled by a spatial dose volume distribution of radiation, the shape of the spatial distribution depending on the specific collimator setting. This include, a) selecting at least one isocenter position within a target; b) evaluating each isocenter based on predetermined conditions; c) selecting at least a specific collimator and sector setting for each isocenter based on the evaluation; d) calculating a dose for the selected isocenters; and e) repeating the step a)-d) until at least one stopping criteria has been reached, wherein a final set of isocenters are provided; and thereafter the final set of isocenters are used in treatment planning.

In embodiments of the present invention, the steps a)-e) further comprises: b) evaluating a predetermined number of columns in a dose rate matrix for each isocenter based on predetermined conditions, wherein each column include a specific collimator and sector setting;
c) selecting at least one column for each isocenter based on the evaluation; d) calculating the dose including the selected isocenters;
e) repeating the steps a)-d) until at least one stopping criteria has been reached, wherein a final set of isocenters are provided; and using the final set of isocenters in treatment planning.

In a further embodiment of the present invention, there is provided a method for dose planning for a radiation therapy system, radiation therapy unit, wherein a spatial dose distribution surrounding the focus point can be changed by adjusting collimator settings, the collimator having a plurality of collimator passage inlets directing radiation emanating from radioactive sources of a source carrier arrangement of the therapy system to a focus point, wherein the collimator is arranged to rotate around an axis along a translational direction of a patient to allowing radiation to be distributed in different angles, the method comprising: obtaining a target volume of a region of a patient to be treated during a treatment of a patient in a radiation therapy unit; selecting a dose level for the planned treatment; determining shots to be delivered during the treatment, each shot being associated with an isocenter and being modelled by a spatial dose volume distribution of radiation, the shape of the spatial distribution depending on the specific collimator setting, including: f) selecting isocenter positions within a target and/or angles in a predetermined angle range; g) evaluating each isocenter and/or angle based on predetermined conditions; h) selecting at least a specific collimator and sector setting for each isocenter and angle based on the evaluation; i) calculating a dose for the selected isocenters; j) repeating the step f)-i) until at least one stopping criteria has been reached, wherein a final set of isocenters and angles are provided; and using the final set of isocenters and/or angles in treatment planning.

In embodiments of the present invention, the steps f)-j) further comprises: g) evaluating a predetermined number of columns in a dose rate matrix for each isocenter and/or angle within a predetermined angle range based on predetermined conditions, wherein each column include a specific collimator and sector setting; h) selecting at least one column for each isocenter and/or angle based on the evaluation; i) calculating the dose including the selected isocenters and/or angles; j) repeating the steps f)-i) until at least one stopping criteria has been reached, wherein a final set of isocenters and/or angles are provided; and using the final set of isocenters and/or angles in treatment planning.

According to embodiments of the present invention, the step of selecting includes keeping the columns for each angle and/or isocenter from the step selected in a prior iteration, removing columns for each angle and isocenter in the selected prior iteration, or removing a subset of columns for each angle and isocenter in the selected prior iteration based on the evaluation.

According to embodiments of the present invention, the step of evaluating comprises evaluating at least one column for each angle and isocenter using a cost function calculation.

$$r_m = c_m - \sum_{l=1}^{N_J} \lambda_l \phi_{lm},$$

where $c_m$ is the coefficient of the objective corresponding to the candidate variable $\lambda_l$ are the Lagrange multipliers from the solution of the master problem, $N_J$ are the number of voxels and $\phi_{lm}$ is an element in the dose rate kernel corresponding to the candidate DOF. In principle, the column with the largest negative reduced cost should be added to the problem. However, since there are in practice 24 columns corresponding to each isocentre in embodiments with a rotatable collimator, the isocentre can be choosed based on a heuristic computed from the reduced costs, such as the sum, a weighted sum or the maximum values.

In embodiments of the present invention, the isocenter and/or angle that results in the largest negative reduced cost in the cost function calculation is selected for dose calculation.

In embodiments of the present invention, the isocenter determination can initialized by choosing a first isocenter according to some criteria, for example the isocenter with the largest negative value of $r_j$, assuming the Lagrange multipliers to be equal to 1.

In embodiments of the present invention, iterations are made until a given stopping criteria is satisfied, i.e. when the heuristic for the best isocentre is below a limit $r_{stop}$ or the number of iterations exceeds a predetermined limit, $n_{max}$.

According to other embodiments, the stopping criteria includes a predetermined number of isocenters, a predetermined number of angles, the number of iterations has reached a predetermined limit and when a relative improvement is below a predetermined level of a cost function has been reached.

In an embodiment of the present invention, there is provided a dose planning software for a radiation therapy system, the radiation therapy system comprising a radiation therapy unit having a fixed radiation focus point, wherein a spatial dose distribution surrounding the focus point can be changed by adjusting collimator settings, the collimator having a plurality of collimator passage inlets directing radiation emanating from radioactive sources of a source carrier arrangement of the therapy system to the focus point, the dose planning computer structure comprising:
  a) selecting at least one isocenter position within a target;
  b) evaluating each isocenter based on predetermined conditions;
  c) selecting at least a specific collimator and sector setting for each isocenter based on the evaluation;
  d) calculating a dose for the selected isocenters;
  e) repeating the step a)-d) until at least one stopping criteria has been reached, wherein a final set of isocenters are provided; and using the final set of isocenters in treatment planning.

In embodiments of the present invention, there is provided a dose planning software for a radiation therapy system, a radiation therapy unit, wherein a spatial dose distribution surrounding the focus point can be changed by adjusting collimator settings, the collimator having a plurality of collimator passage inlets directing radiation emanating from radioactive sources of a source carrier arrangement of the therapy system to a focus point, wherein the collimator is arranged to be rotatable around an axis along a translational direction of a patient to allow radiation to be distributed in different angles to said focus point, the method comprising: obtaining a target volume of a region of a patient to be treated during a treatment of a patient in a radiation therapy unit; selecting an dose level for the planned treatment; determining shots to be delivered during the treatment, each shot being associated with an isocenter and being modelled by a spatial dose volume distribution of radiation, the shape of the spatial distribution depending on the specific collimator setting, including:
  f) selecting isocenter positions within a target and/or angles in a predetermined angle range;
  g) evaluating each isocenter and/or angle based on predetermined conditions;
  h) selecting at least a specific collimator and sector setting for each isocenter and/or angle based on the evaluation;
  i) calculating a dose for the selected isocenters;
  j) repeating the steps until at least one stopping criteria has been reached, wherein a final set of isocenters and angles are provided; and using the final set of isocenters and/or angles in treatment planning.

In certain embodiments, the predetermined angle range for a sector is 45 degrees. For example, the angle range could be between 0-45 degrees, or −22.5 and 22.5 degrees or any other suitable range.

As the skilled person realizes, steps of the methods according to the present invention, as well as preferred embodiments thereof, are suitable to realize as computer program or as a computer readable medium.

Further objects and advantages of the present invention will be discussed below by means of exemplifying embodiments.

DETAILED DESCRIPTION OF THE DRAWINGS

Figure 1A:
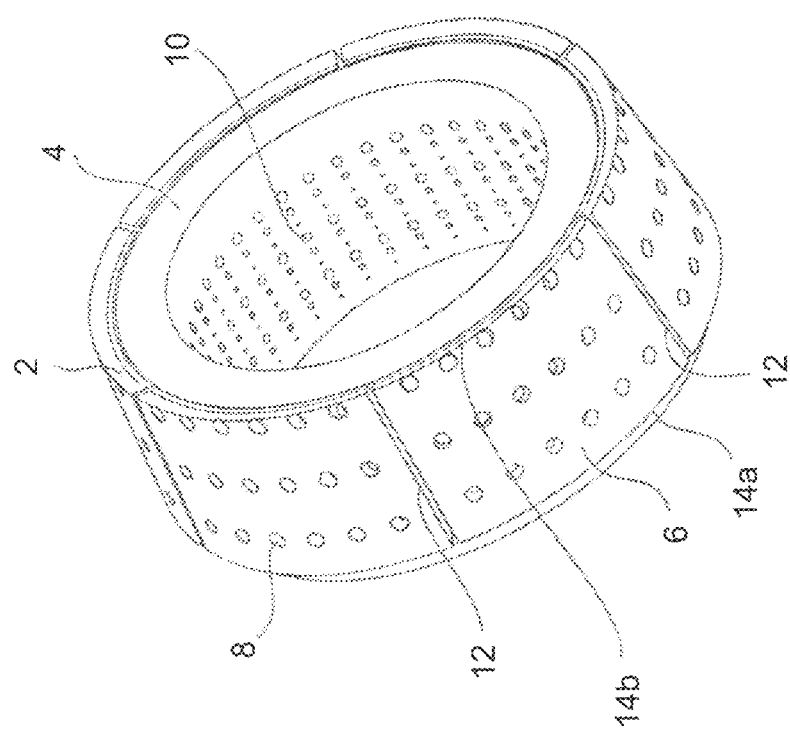
FIG. 1a is a perspective view of an assembly comprising a source carrier arrangement surrounding a collimator body in which the present invention may be used.
Figure 1B:
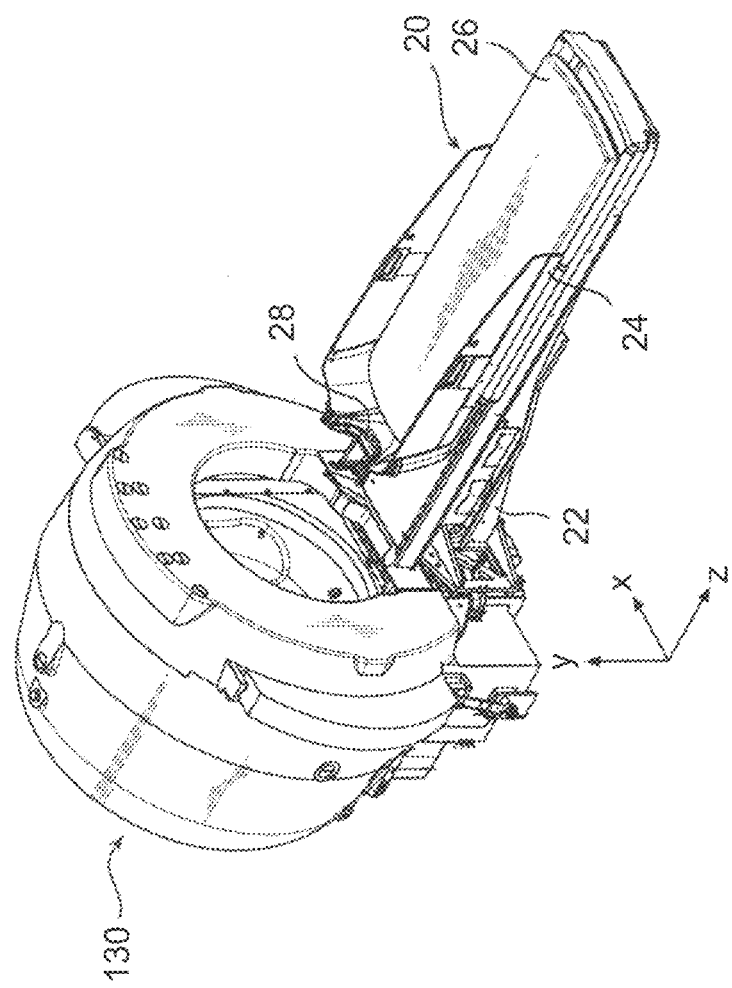
FIG. 1b shows a radiation therapy device in which the assembly of FIG. 1 may be used.

With reference first to FIGS. 1a and 1b, an exemplary radiation therapy device in which a treatment plan developed using the present invention can be used for treatment of a patient.

FIG. 1a is a perspective view of an assembly comprising a source carrier arrangement 2 surrounding a collimator body 4. The source carrier arrangement 2 and the collimator body 4 both have the shape of a frustum of a cone. The source carrier arrangement 2 comprises six segments 6 distributed along the annular circumference of the collimator body 4. Each segment 6 has a plurality of apertures 8 into which containers containing radioactive sources, such as cobalt, are placed. The collimator body 4 is provided with collimator passages or channels, internal mouths 10 of the channels are shown in the figure.

Each segment 6 has two straight sides 12 and two curved sides 14a, 14b. One of the curved sides 14a forms a longer arc of a circle, and is located near the base of the cone, while the other curved side 14b forms a shorter arc of a circle. The segments 6 are linearly displaceable, that is they are not rotated around the collimator body 4, but are instead movable back and forth along an imaginary line drawn from the center of the shorter curved side 14b to the center of the longer curved side 14a. Such a translation displacement has the effect of a transformation of coordinates in which the new axes are parallel to the old ones.

As can be seen from FIG. 1a there is a larger number of internal mouths 10 or holes of the collimator passages than the number of aperture 8 for receiving radioactive sources. In this particular case, there are three times as many collimator passages as there are apertures for receiving radioactive sources, such as e.g. 180 apertures and 540 collimator passages. The reason for this is that there are three different sizes of collimator passages in the collimator body 4, or rather passages which direct radiation beams with three different diameters, toward the focus point. The diameters may e.g. be 4, 8 and 16 mm. The three different types of collimator passages are each arranged in a pattern which corresponds to the pattern of the apertures in the source carrier arrangement. The desired size or type of collimator passage is selected by displacing the segments 6 of the source carrier arrangement linearly along the collimator body so as to be in register with the desired collimator passages.

In FIG. 1*b*, a radiation therapy system including a radiation therapy device 130 having a source carrier arrangement as shown in FIG. 1*b*, and a patient positioning unit 20 is shown. In the radiation therapy unit 130, there are thus provided radioactive sources, radioactive source holders, a collimator body, and external shielding elements. The collimator body comprises a large number of collimator channels directed towards a common focus point, as shown in FIG. 1*b*.

The patient positioning unit 20 comprises a rigid framework 22, a slidable or movable carriage 24, and motors (not shown) for moving the carriage 24 in relation to the framework 22. The carriage 24 is further provided with a patient bed 26 for carrying and moving the entire patient. At one end of the carriage 24, there is provided a fixation arrangement 28 for receiving and fixing a patient fixation unit or interface unit. The coordinates of the fixation unit are defined by a fixation unit coordinate system, which through the fixed relationship with the treatment volume also is used for defining the outlines of the treatment volume. In operation, the fixation unit, and hence the fixation unit coordinate system, is moved in relation to the fixed radiation focus point such that the focus point is accurately positioned in the intended coordinate of the fixation unit coordinate system.

Figure 2:
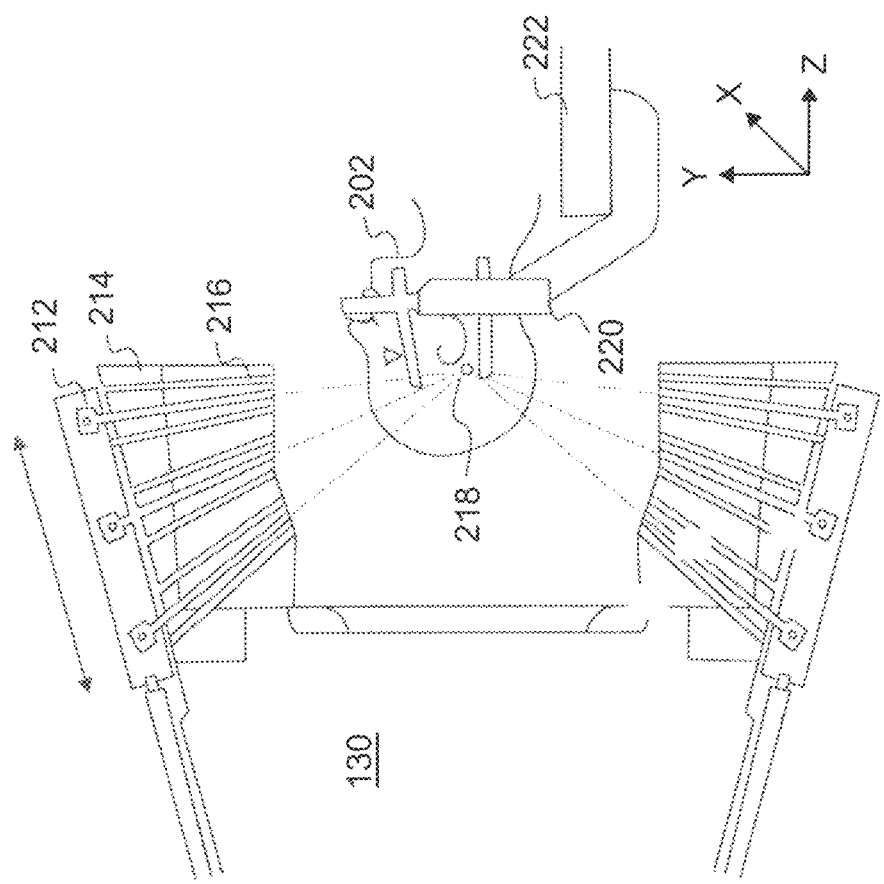
FIG. 2 shows a radiation therapy device, a Gamma Knife, in which the present invention may be used.

FIG. 2 illustrates a radiation therapy device 130, a Gamma Knife in which the present invention can be used. A patient 202 may wear a coordinate frame 220 to keep stable the patient's body part (e.g. the head) undergoing surgery or radiation therapy. Coordinate frame 220 and a patient positioning system 222 may establish a spatial coordinate system, which may be used while imaging a patient or during radiation surgery. Radiation therapy device 130 may include a protective housing 214 to enclose a plurality of radiation sources 212 for generation of radiation beams (e.g. beamlets) through beam channels 216. The plurality of beams may be configured to focus on an isocenter 218 from different locations. While each individual radiation beam may have relatively low intensity, isocenter 218 may receive a relatively high level of radiation when multiple doses from different radiation beams accumulate at isocenter 218. In certain embodiments, isocenter 218 may correspond to a target under surgery or treatment, such as a tumour.

In further embodiments of the present invention, it is used in a radiation therapy device provided with a collimator body that is rotatable around the z-axis or around an axis along the translational direction of the patient.

Figure 3B:
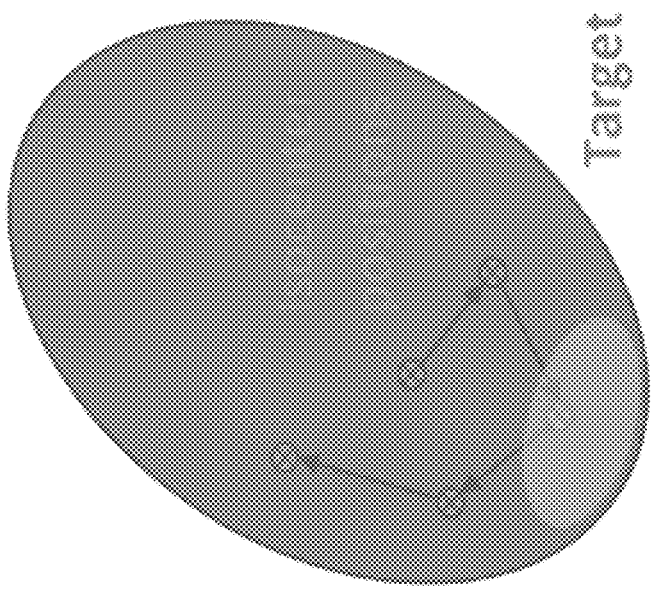
FIGS. 3a and 3b is simplified illustrations of positioning of isocenter positions.
Figure 3A:
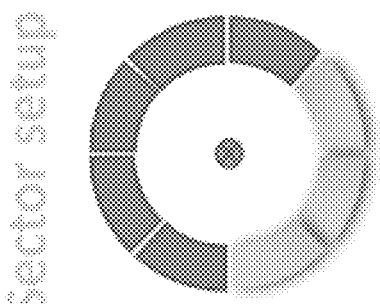

During the treatment, the patient can be moved so that the isocenter 218 of the radiation therapy device 130 is positioned in one of a number of predetermined isocenter positions. These positions are typically placed inside the lesion of the patient. Beam delivery is only allowed while the patient is in a stationary position, the collimators are then blocked to allow the reposition to a new isocenter position, this is illustrated in FIG. 3*a* and FIG. 3*b*. In every isocenter position, radiation can be delivered through each set of collimators, from every sector independently. The result is referred to as an LGK "shot", and there is a high amount of shot variations, i.e., DoFs. In some situations, it might be beneficial to have a number of sectors completely blocked during treatment in an isocenter position if, e.g., radiation would need to travel through an organ at risk ("OAR"). Prior to treatment planning the important structures, both tumour and OARs, need to be segmented. Given this information, the control inputs for the LGK must be carefully designed so that the optimal treatment is administered. The result is referred to as a treatment plan and is generated often using software. One such software is called Leksell GammaPlan® (LGP).

A technique for radiation treatment planning is called inverse planning. In co-pending patent application by the same applicant, inverse planning methods are described in which the present invention can be used, for example, U.S. 62/633,437 and U.S. 62/633,418.

To calculate the dose in the volume or target, it will be assumed that the dose rate from the radioactive sources is time-invariant during the treatment. The variation of the activity during the duration of a treatment is negligible due to the fact that Co-60 has a half-life of 5-27 years. Now, let $\phi_{cs}(x, \xi)$ denote the dose accumulation rate in the point x resulting from irradiating trough sector s and collimator c in an isocenter position $\xi$. The total dose d(x) in a point resulting from a shot in the isocenter, with all sectors and collimators, can then be expressed as $$d(x) = \sum_{c=1}^{3} \sum_{s=1}^{8} \phi_{cs}(x, \xi) \cdot t_{cs} \qquad \text{(Eqt. 1)}$$

The dose rates $\phi_{cs}$ may be calculated, for example using the TMR-algorithm described in Elekta: A new TMR dose algorithm in Leksell GammaPlan. 2011. White Paper: Article no. 1021357.00. In this model the head is assumed to be homogeneous and entirely made out of water. To reduce the number of expensive computations, translation invariance is assumed. This means that one can reuse the dose distribution calculated in one central position $\xi^* X_T$ for every isocenter in the tumour $\xi_i$, $i \in \{1, \ldots, N_{isoc}\}$ where $N_{isoc}$ is the total number of isocenters, just by repositioning according to $$\phi_{cs}(x,\xi_i) \approx k_{csi} \cdot \phi_{cs}(x+(\xi^*-\xi_i)\xi^*) \qquad \text{(Eqt. 2)}$$

where $k_{csi}$ is a rescaling constant for adjustments. This scaling constant can be determined by just calculating the center dose for the desired isocenter according to $$k_{csi} = \phi_{cs}(\xi_i,\xi_i)/\phi_{cs}(\xi^*,\xi^*) \qquad \text{(Eqt. 3)}$$

The resulting dose calculation from (1) can then be written as a simple matrix vector multiplication according to $$d_j = \sum_{c=1}^{3} \sum_{s=1}^{8} \sum_{i=1}^{I} \phi_{cs}(x_j, \xi_i) \cdot t_{csi} \to d = \Phi t \qquad \text{(Eqt. 4)}$$

The matrix element $\phi_{j,csi} = \phi_{cs}(x_j, \xi_i)$ contains the dose rate from the known configuration with the voxels j corresponding to the rows and the DoFs to the columns. The total number of DoFs becomes $F=3\times 8\times N_{isoc}$. All the known information is then contained inside the matrix $\phi \in R^{N_{is\,j}\times F}$ that can be calculated in advance; this matrix will be referred to as the dose rate matrix (DRM).

A penalty based cost function can be used that evaluates the distribution of dose d in the $N_J$ voxels along with the times t spent in the F different DOFs. The dose d(t) is in turn a function of the beam-on times in ($_4$). An objective can then be determined as described in "A linear programming approach to inverse planning in Gamma Knife radiosurgery", J. Sjolund, S. Riad, M. Hennix and H. Nordstrom, (2019), Med. Phys., Accepted author manuscript, doi:

10.1002/mp.13440, and in the thesis work "Gamma Knife treatment planning with new degrees of Freedom"; by E. Norell, KTH Royal Institute of Technology, School of Engineering Sciences.

When a plan has been generated from the optimization, the dose to all voxels must be computed. The clinical evaluation is done in terms of metrics that are related to the objectives in the optimization but not directly proportional to them. However, these metrics are typically non-convex. $X_p$ denotes the planning isodose volume, i.e., the volume that is receiving a dose d≥$D_T$ in the treatment plan. In the ideal case $X_P=X_T$, where $X_T$ is the target volume, meaning that no other tissue except the tumour receives a dose exceeding the prescription dose. In practice, this is not possible, therefore, let V (V(·): $R^3 \to R$) denote the volume of a set and define.

$$\text{Coverage} = \frac{V(X_T \cap X_P)}{V(X_T)} \quad \text{(Eqt. 5)}$$

which measure how large share of the target that receives a dose as high as the prescribed dose. Furthermore, it is also important to make sure that not too much dose is leaking out to healthy tissue, why we define $$\text{Selectivity} = \frac{V(X_T \cap X_P)}{V(X_P)} \quad \text{(Eqt. 6)}$$

that describes how much of the volume receiving the prescription dose that is actually the target. A good plan requires a balance between these metrics, which can be emphasized by considering the Paddick conformity index: PI=Coverage×Selectivity (described in I. Paddick. A simple scoring ratio to index the conformity of radiosurgical treatment plans. Journal of Neurosurgery, 2000). The goal is that these three measures should be as close to 1 as possible. Moreover, the dose should drop quickly outside the target, which would indicate that adjacent tissue is being spared. Let V ($X_{P/j}$) be the volume receiving at least half of the prescription dose. Define the gradient index as $$\text{Gradient index:} = \frac{V(X_{P/2})}{V(X_P)} \quad \text{(Eqt. 7)}$$

as a measure of how steeply the dose drops to half the prescription dose.

The present invention preferably uses the assumption of rotational invariance. This means that the dose distribution ϕ is rotation invariant. In other words, when rotating the sources, the distribution form is preserved but rotated accordingly. Since there are 8 sectors, each assumed to be identical, there is no reason to rotate the collimator body more than, or equal to, a total of 45 degrees. Moreover, as mentioned above, rotation invariance is an assumption and is likely to become less accurate for bigger rotations. For that reason, it is natural to only allow rotations between −22.5 and 22.5 degrees to minimize the effect of the assumption.

There is an infinite number of potential DoFs that could be incorporated into the model, but the improvement they offer can vary greatly. Column generation can be employed to locate the most significant DoFs before they are allowed into the model.

Now, an approach will be described that proposes a measure that can evaluate the potential benefit of the entire group of columns, corresponding to an angle and an isocenter position, without reducing them to primitive shots. In the approach described below, it should be noted that both angle and/or isocenter position can be varied. That is, the angle can be held fixed and the isocenter can be varied, the isocenter can be fixed and the angle varied, and both can be varied. This provides a high degree of flexibility. For example, the optimization can be used with present Gamma Knife where the collimator body is fixed as well as in modified version where the collimator body may be rotated around the z-axis.

Consider the solution where only the best collimator in every sector is used, whereas in a regular shot one could of course use all of them if beneficial. A heuristic approach is to evaluate them all as one unit, where only the beneficial columns are included. The latter is due to that any unfavorable DoF can simply be turned off in practice, anyway. Therefore, the generalized reduced cost for a single position can be evaluated as:

$$r_{ai} = \sum_{cs} \max\left\{\sum_j \lambda_j \cdot \phi_{cs}(x_j, \theta_a, \xi_i), 0\right\} = c - \sum_{cs} [\lambda^T \Phi_{i,csa}]_+ \quad \text{(Eqt. 8)}$$

Where $\theta_a$ is the rotation angle of the collimator body and $x_j$ is the spatial coordinate for voxel j. Then, in the ideal case the program would be solved according to, $$\min_{\theta,\xi} \; c - \sum_{cs}\left[\sum_j \lambda_j \cdot \phi_{cs}(x_j, \theta_a, \xi_i)\right]_+ \quad \text{(Eqt. 9)}$$
$$\text{s.t. } \theta_a \in (-22.5, 22.5]$$
$$\xi_i \in X_T$$

and the angle and isocenter that produces that least reduced cost are found.

An efficient way of approximating a solution of this non-convex problem is to generate a large set of $\theta^Q$ with Q of candidate angles and a set of M isocenter position candidates Y and then choose between these to include in the optimization. In principle the set of candidate angles or candidate isocenters can contain only one element, corresponding to a fixed angle and isocenter, respectively. The best candidate angle and isocenter could then be found by solving $$\left\{(SUB)_{\underset{a,i}{\text{argmin}}} \; c - \sum_{cs}\left[\sum_j \lambda_j \cdot \phi_{cs}(x_j, \theta_a, \xi_i),\right]_+ \atop \text{s.t. } \theta_a \in \Theta^Q \atop \xi_i \in Y\right\} \quad \text{(Eqt. 10)}$$

This procedure can then be reduced to a number of dot product computations:

$$(SUB)_{\underset{a,i}{argmin}} \left\{ \sum_{cs} [\lambda^T \cdot \Phi_{i,csa}]_+ \right\}_{a=1,\ldots,Q, i=1,\ldots,M} \quad \text{(Eqt. 11)}$$

The result from Eqt. 11 is a proposal which candidate angle and isocenter has the highest potential of improving the solution.

Now, the models used in the present invention will be discussed. Regarding the modelling of rotational DoF, three variations is detailed. A firm foundation is laid by a uniform model where angle nodes are spread out evenly over the interval, and equally for all isocenters.

In order to reduce the number of voxels present in the problem, for example, representative subsampling or clustering can be utilized. Representative subsampling has been described in a co-pending patent application by the same applicant. The clustering procedure will be described below. A so-called K-means algorithm is employed for the voxels of every structure independently. An approach based on clustering of voxels in an IMRT framework has been explored in "Real-time radiation treatment planning with optimality guarantees via cluster and bound methods", B. Ungun, L. Xing, and S. Boyd., INFORMS Journal on Computing, 2018, with promising results. The overarching idea is similar to that of representative sub-sampling: there is a lot of redundant information in the data and far from all of it is necessary to obtain a good plan. The clustering algorithm differentiates itself by grouping, i.e. clustering, data in such a way that a minimal amount of important information is lost. It is emphasized that the data is grouped using the information of all the members to represent the whole group. This, however, comes at a cost of time and computation load, in contrast to representative sub-sampling where the data is sampled randomly, and the remaining information is discarded.

According to an embodiment, the clustering is done as follows: the voxels can be distributed over a predetermined set of clusters $$K = \{1, \ldots, N_K\} \quad \text{(Eqt. 12)}$$

The relation between clusters and voxels is described by a matrix $$U \in \{0,1\}^{N_J \times N_K} \quad \text{(Eqt. 13)}$$

where $$U_{jk} \in \{0,1\} \quad \text{(Eqt. 14)}$$

indicates whether voxel j in the voxel set J belongs to cluster k or not. Define $$C_k = \{j \in J : U_{jk} = 1\} \quad \text{(Eqt. 15)}$$

to be the indices of the voxels that belong to cluster k. It is assumed that the dose in the cluster $d_k$ is uniform and it can generally be represented by any convex function of the member voxel doses, but most commonly it is defined as the average according to $$d_k = \sum_{csi} \hat{\Phi}_{k,csi} \cdot t_{csi} = \frac{1}{|C_k|} \sum_{j \in C_k} \sum_{csi} \Phi_{j,csi} t_{csi} \quad \text{(Eqt. 16)}$$

The goal is to produce a reduced matrix $\hat{\phi}$ such that $U\hat{\phi} \approx \phi$. Note that, due to the sparse nature of U, the average dose from Eqt. 16 also can be expressed as $$\hat{\phi} = (U)^{-1} U^T \phi \quad \text{(Eqt. 17)}$$

An optimization problem with U as a variable can be proposed with the goal to minimize the $L_2$ matrix norm according to $$(K) \underset{U}{\min} \|\Phi - U\hat{\Phi}\|_2 \quad \text{(Eqt. 18)}$$

$$\text{s.t. } \hat{\Phi} = (U^T U)^{-1} U^T \Phi$$

$$\sum_k U_{jk} = 1, \forall j$$

$$U_{jk} \in \{0,1\}, j = 1, \ldots, N_J, k = 1, \ldots, N_K$$

This must be done separately for the voxels in every structure T, S, L (T for target, and S and L for auxiliary structures) to ensure clusters are not made from voxels in different volumes. Note that the OAR structure is not clustered but may be clustered. However, the problem Eqt. 18 is NP-hard and one typically has to resort to some heuristic. In this case we use the K-means algorithm (described in B. Ungun, L. Xing, and S. Boyd. Real-time radiation treatment planning with optimality guarantees via cluster and bound methods. To appear, INFORMS Journal on Computing, 2018) according to the procedure:

(1). Calculate centroids: $\hat{\phi} = (U^T U)^{-1} U^T \phi$ (2). Compute uninitialized distance matrix: $D = -2\hat{\phi}\phi^T + \text{diag}(\hat{\phi}^T\hat{\phi})^T$ $$(3). \ u_{jk} = \begin{cases} 1, & k = \text{argmin}\{d_{jk}\} \\ 0, & \text{otherwise} \end{cases},$$

$$j = 1, \ldots, N_J, k = 1, \ldots, N_K$$

These steps (1)-(3) are repeated until a stable solution has been reached or until an iteration limit has been reached. Note that a starting guess of clusters is necessary to start the algorithm.

Hence, applying the above described K-means algorithm for clustering, a number of cluster sets are given. Every cluster is weighted with the number of voxels it contains. Given the high dose gradient nature of the Leksell Gamma Knife®, alternate approaches to clustering with emphasis on surface voxels may also be used. There are presumably significantly higher dose gradients close to the surface and thus a finer mesh of clusters might be necessary there to generate good plans. A number of different cluster approaches can be applied in the present invention:

A: Normal full clustering: The target, inner ring and outer ring are clustered independently with different fractions.

B: Surface independent clustering: The target surface voxels are clustered independently of the core voxels.

C: Surface exclusive clustering: Discard the target core voxels entirely and cluster the surface exclusively.

The distribution of angles and/or isocenter positions is not necessarily uniform. To determine the isocenter positions and corresponding angles, the column generation method described above in Eqt. 8-Eqt. 11 can be used. The aim is to improve the cost function with the smallest number of DoFs in the model. For example, the following can be applied:

$$\underset{t}{\min} f(d, t) \quad \text{(Eqt. 19)}$$

-continued $$\text{s.t.} \quad d_j = \sum_{csai} \phi_{cs}(x_j, \xi_i, \theta_{ai}) \cdot t_{csai},$$

$$\theta_{ai} \in \theta_\beta^Q, \forall a, i$$

$$d \in D, t \geq 0$$

Here, $\theta_\beta^Q$ is a uniform set of candidate angles, and $\beta$ is an index set indicating which of the candidates that are allowed to be used, which is determined according to Eqt. 11.

The algorithm below describes how the procedure is iterated to improve the objective, while at the same time increasing the problem size, until the candidates run out.
(1). Start with $\beta$ so that $\theta_\beta = \{0\}, \forall i$
(2). Solve Eqt. 19 and acquire $\lambda$
(3). Update $\beta$ with $$a = \mathop{\text{argmax}}_{a,i} \left\{ \sum_{cs} [\Phi_{i,csa}^T \lambda]_+ \right\}_{a=1,\ldots,Q, i=1,\ldots,M}, \forall i$$

(4.) Repeat step (2) and (3) until a maximum of $|\beta|$ has been reached. Note that if the algorithm is iterated until all candidates are included, the result will be equivalent to a uniform model, but at a much higher computational cost. Therefore, it is of interest to define a maximum of iterations that is less than Q. One way is to examine the improvements of the cost function and break when a certain level of diminishing returns is reached.

Figure 4:
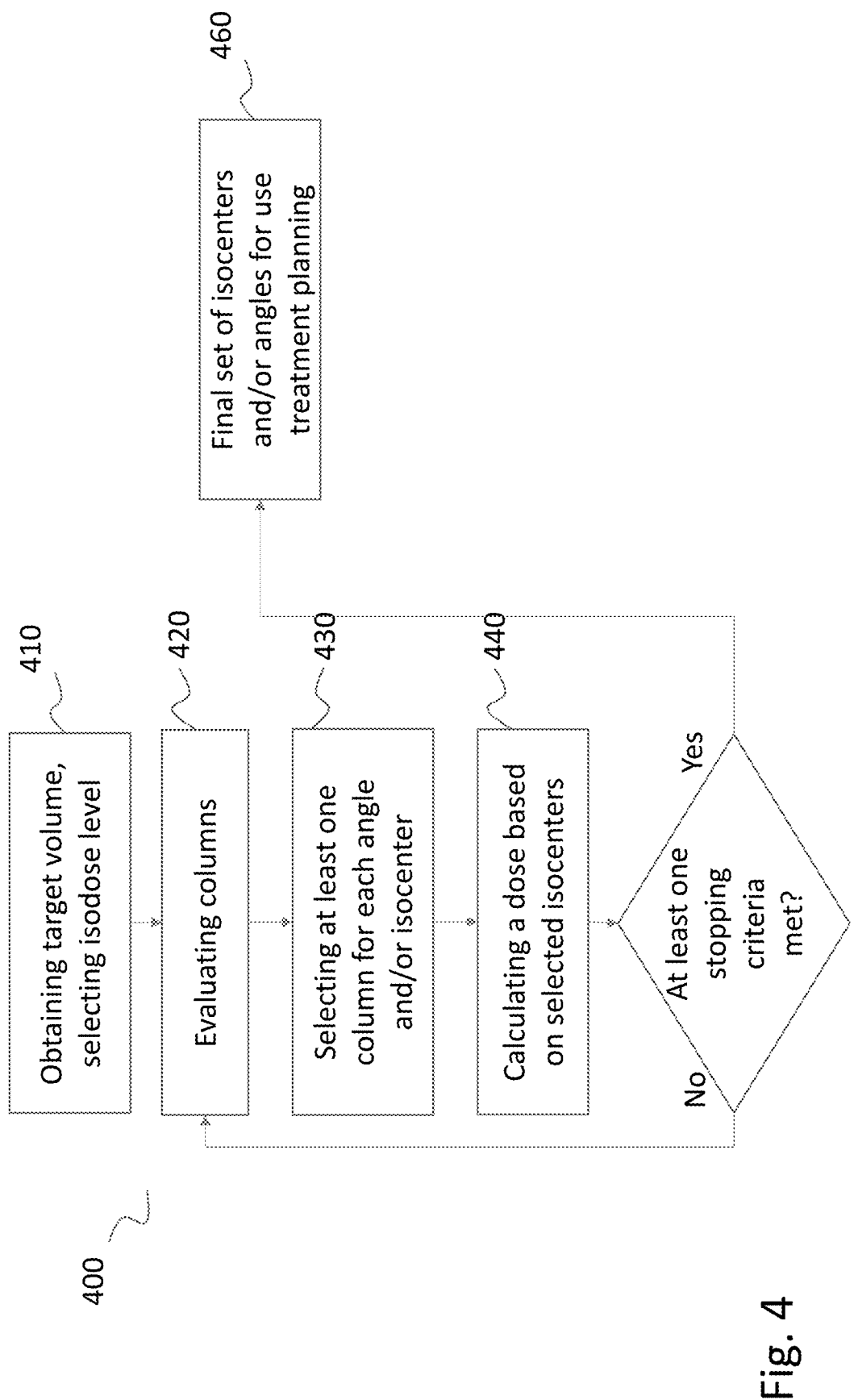
FIG. 4 is a flow diagram illustrating an embodiment of the present invention.

With reference now to FIG. 4, a general method 400 according to the present invention will be described. Preferably, the method is used in treatment planning for radiation therapy systems such as the Leksell Gamma Knife®. The collimator body is provided with several groups or sets of collimator passages, each set being designed to provide a radiation beam of a respective specified cross-section toward a fixed focus point. Suitably the inlet of each set of collimator passages has a pattern that essentially corresponds to the pattern of the sources on the source carrier arrangement. These sets of collimator passage inlets may be arranged so that it is possible to change from one set to another, thereby changing the resulting beam cross-section and the spatial dose distribution surrounding the focus point. The number of sets of collimator passages with different diameter may be more than two, such as three or four, or even more. A typical embodiment of the collimator comprises eight sectors each having four different states (beam-off, 4 mm, 8 mm, and 16 mm). The sectors can be adjusted individually, i.e. different states can be selected for each sector, to change the spatial distribution of the radiation about the focus point.

First in the method 400, at step 410 a target volume of a region of a patient to be treated during a treatment of a patient in a radiation therapy unit may be obtained. A dose level for the planned treatment may be selected and determining shots to be delivered during the treatment, each shot being associated with an isocenter and being modelled by a spatial dose volume distribution of radiation, the shape of the spatial distribution depending on the specific collimator setting and the selected dose level. In step 420, it is evaluated a predetermined number of columns in a dose rate matrix for each isocenter and/or predetermined angle in a predetermined angle range based on predetermined conditions, wherein each column include a specific collimator and sector setting. Then, at step 430, at least one column, in practice 24 columns, for each isocenter and/or angle is selected based on the evaluation. At step 440, the dose is calculated including the selected isocenters and/or angles. Thereafter, at step 450, it is checked whether at least one stopping criterion has been reached. If yes, the procedure 400 proceeds to further treatment planning using the final set of isocenters and/or angles. On the other and if no, the procedure returns to step 420.

In embodiments, the step of selecting 430 includes keeping the columns for each isocenter and/or angle from the step selected in a prior iteration, removing columns for each angle and isocenter in the selected prior iteration, or removing a subset of columns for each isocenter and/or angle in the selected prior iteration based on the evaluation.

The step of evaluating 420 may comprise calculating the value of a reduced cost for each column and the step of selecting comprises selecting the column for each angle and isocenter that results in the largest negative reduced cost in the cost function calculation. In embodiments, the reduced cost is defined as $$r_m = c_m - \sum_{l=1}^{N_j} \lambda_l \phi_{lm},$$

where $c_m$ is the coefficient of an objective of the variable $x_j$, $\lambda_i$ are Lagrange multipliers and $\phi_{im}$, is a dose rate kernel corresponding to the isocenter and the dose rate in a voxel j as a result of irradation with the DoF m, $N_j$ are the number of voxels and $P_{lm}$ is an element in the dose rate kernel corresponding to the candidate DOF.

The stopping criteria include a predetermined number of isocenters, a predetermined number of angles, the number of iterations has reached a predetermined limit and when a predetermined level of a cost function has been reached or predetermined limit on the improvement of the cost function.

Figure 5:
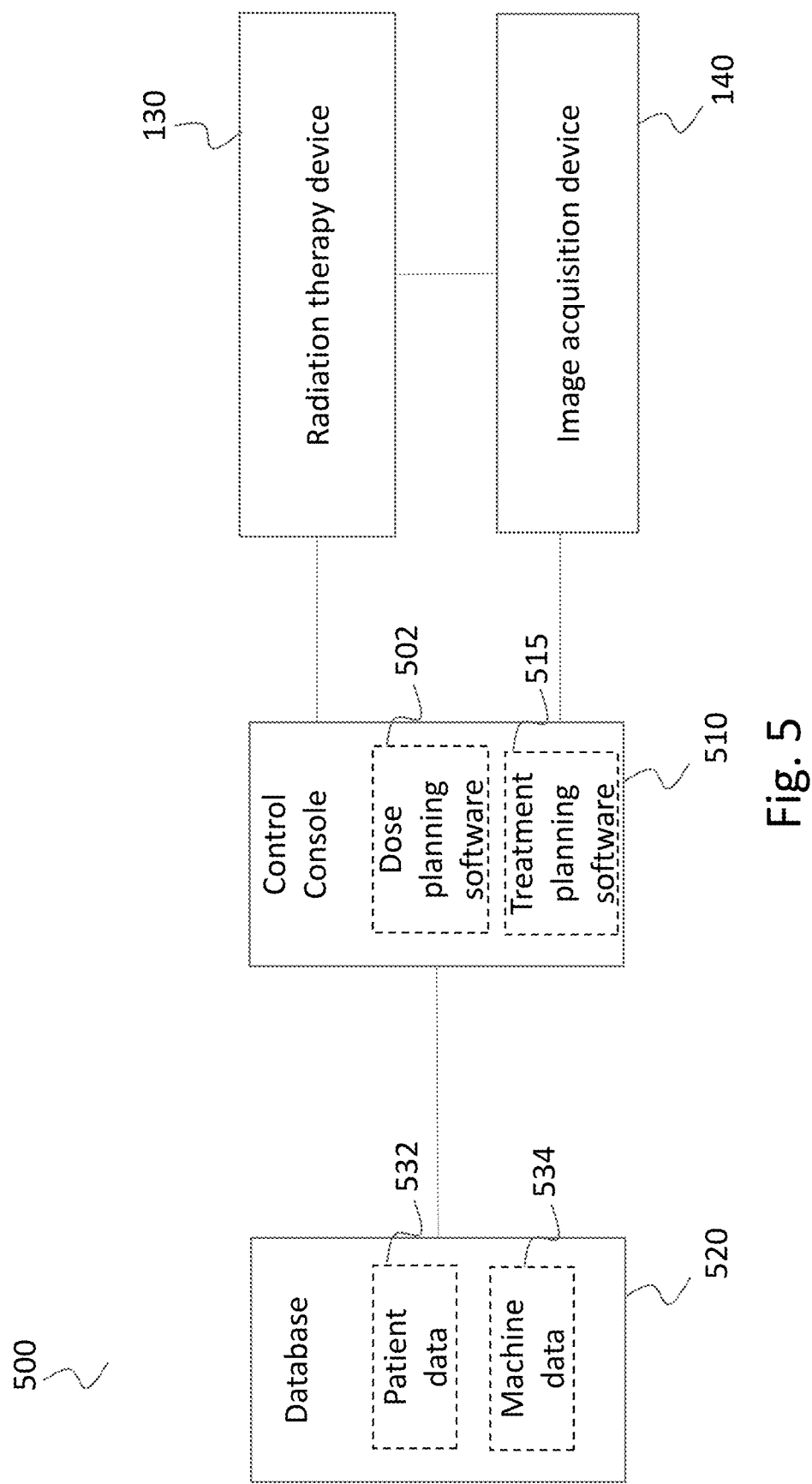
FIG. 5 is a block diagram showing an exemplary radiation therapy system 500 according to some embodiments of the present invention.

Turning now to FIG. 5, a dose planning computer structure or software 502 in which the method according to the present invention may be implemented will be described. The dose planning structure or software 502 may be included in a radiation therapy system 500 as shown in FIG. 5. As shown in FIG. 5, radiation therapy system 500 may include a control console 510, a database 520, a radiation therapy device 130. The control console 510 may include hardware and software components to control radiation therapy device 130 and an image acquisition device 140 and/or to perform functions or operations such as treatment planning using a treatment planning software and dose planning using dose planning computer structure or software 502, treatment execution, image acquisition, image processing, motion tracking, motion management, or other tasks involved in a radiation therapy process. The hardware components of control console 510 may include one or more computers (e.g., general purpose computers, workstations, servers, terminals, portable/mobile devices, etc.); processor devices (e.g., central processing units (CPUs), graphics processing units (GPUs), microprocessors, digital signal processors (DSPs), field programmable gate arrays (FPGAs), special-purpose or specially-designed processors, etc.); memory/storage devices (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); or other suitable hardware. The software components of control console 500 may include operation system software, application software, etc. For example, as shown in FIG. 5, control console 510 includes the dose planning computer structure or software 502 and a treatment planning/delivery software 515 that both may be stored in a memory/storage device of control console 510. Software 502 and 515 may include computer readable and executable codes or instructions for performing the processes described in detail in this application. For example, a processor device of control console 510 may be communicatively connected to a memory/storage device storing software 502 and 515 to access and execute the codes or instructions. The execution of the codes or instructions may cause the processor device to perform operations to achieve one or more functions consistent with the disclosed embodiments.

The treatment planning computer structure or software 502 be configured to execute the methods described herein, for example, the method described with reference to FIG. 3. That is, it may be configured to determine shots to be delivered during the treatment, each shot being associated with an isocenter and being modelled by a spatial dose volume distribution of radiation, the shape of the spatial distribution depending on the specific collimator setting and the selected dose level, including: evaluating each isocenter and predetermined angle in a predetermined angle range based on predetermined conditions; selecting at least a specific collimator and sector setting for each isocenter and angle based on the evaluation; calculating a dose rate for the selected isocenters; repeating the steps evaluating, selecting and calculating until at least one stopping criterion has been reached, wherein a final set of isocenters and angles are provided. The final set of isocenters and angles may thereafter be in treatment planning, for example, in the treatment planning software 515. Further, the dose planning software 502 may be configured to evaluating a predetermined number of columns in a dose rate matrix for each isocenter and predetermined angle in a predetermined angle range based on predetermined conditions, wherein each column include a specific collimator and sector setting; selecting at least one column for each isocenter and angle based on the evaluation; calculating the dose rate matrix including the selected isocenters; and repeating the steps evaluating, selecting and calculating until at least one stop criteria has been reached, wherein a final set of isocenters and angles are provided. Thereafter, the final set of isocenters and angles may be used in treatment planning in the treatment planning software 515.

Control console 510 may be communicatively connected to a database 520 to access data. In some embodiments, database 520 may be implemented using local hardware devices, such as one or more hard drives, optical disks, and/or servers that are in the proximity of control console 510. In some embodiments, database 520 may be implemented in a data center or a server located remotely with respect to control console 510. Control console 510 may access data stored in database 520 through wired or wireless communication.

Database 520 may include patient data 532. Patient data may include information such as (1) imaging data associated with a patient anatomical region, organ, or volume of interest segmentation data (e.g., MRI, CT, X-ray, PET, SPECT, and the like); (2) functional organ modeling data (e.g., serial versus parallel organs, and appropriate dose response models); (3) radiation dosage data (e.g., may include dose-volume histogram (DVH) information); or (4) other clinical information about the patient or course of treatment.

Database 520 may include machine data 524. Machine data 524 may include information associated with radiation therapy device 130, image acquisition device 140, or other machines relevant to radiation therapy, such as radiation beam size, arc placement, on/off time duration, radiation treatment plan data, multi-leaf collimator (MLC) configuration, MRI pulse sequence, and the like.

Image acquisition device 140 may provide medical images of a patient. For example, image acquisition device 140 may provide one or more of MRI images (e.g., 2D MRI, 3D MRI, 2D streaming MRI, 4D volumetric MRI, 4D cine MRI); Computed Tomography (CT) images; Cone-Beam CT images; Positron Emission Tomography (PET) images; functional MRI images (e.g., fMRI, DCE-MRI, diffusion MRI); X-ray images; fluoroscopic images; ultrasound images; radiotherapy portal images; Single-Photo Emission Computed Tomography (SPECT) images; and the like. Accordingly, image acquisition device 140 may include an MRI imaging device, a CT imaging device, a PET imaging device, an ultrasound imaging device, a fluoroscopic device, a SPECT imaging device, or other medical imaging devices for obtaining the medical images of the patient.

Radiation therapy device 130 preferably includes a Leksell Gamma Knife®.

Various operations or functions are described herein, which may be implemented or defined as software code or instructions. Such content may be directly executable ("object" or "executable" form), source code, or difference code ("delta" or "patch" code). Software implementations of the embodiments described herein may be provided via an article of manufacture with the code or instructions stored thereon, or via a method of operating a communication interface to send data via the communication interface. A machine or computer readable storage medium may cause a machine to perform the functions or operations described, and includes any mechanism that stores information in a form accessible by a machine (e.g., computing device, electronic system, and the like), such as recordable/non-recordable media (e.g., read only memory (ROM), random access memory (RAM), magnetic disk storage media, optical storage media, flash memory devices, and the like). A communication interface includes any mechanism that interfaces to any of a hardwired, wireless, optical, and the like, medium to communicate to another device, such as a memory bus interface, a processor bus interface, an Internet connection, a disk controller, and the like. The communication interface can be configured by providing configuration parameters and/or sending signals to prepare the communication interface to provide a data signal describing the software content. The communication interface can be accessed via one or more commands or signals sent to the communication interface.

The present disclosure also relates to a system for performing the operations herein. This system may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CDROMs, and magnetic-optical disks, read-only memories (ROMs), random access memories (RAMs), EPROMs, EEPROMs, magnetic or optical cards, or any type of media suitable for storing electronic instructions, each coupled to a computer system bus.

The order of execution or performance of the operations in embodiments of the present disclosure illustrated and described herein is not essential, unless otherwise specified. That is, the operations may be performed in any order, unless otherwise specified, and embodiments of the present disclosure may include additional or fewer operations than those disclosed herein. For example, it is contemplated that executing or performing a particular operation before, contemporaneously with, or after another operation is within the scope of aspects of the present disclosure.

Embodiments of the present disclosure may be implemented with computer-executable instructions. The computer-executable instructions may be organized into one or more computer-executable components or modules. Aspects of the present disclosure may be implemented with any number and organization of such components or modules. For example, aspects of the present disclosure are not limited to the specific computer-executable instructions or the specific components or modules illustrated in the figures and described herein. Other embodiments of the present disclosure may include different computer-executable instructions or components having more or less functionality than illustrated and described herein.

When introducing elements of aspects of the present disclosure or the embodiments thereof, the articles "a," "an," "the," and "said" are intended to mean that there are one or more of the elements. The terms "comprising," "including," and "having" are intended to be inclusive and mean that there may be additional elements other than the listed elements.

Having described aspects of the present disclosure in detail, it will be apparent that modifications and variations are possible without departing from the scope of aspects of the present disclosure as defined in the appended claims. As various changes could be made in the above constructions, products, and methods without departing from the scope of aspects of the present disclosure, it is intended that all matter contained in the above description and shown in the accompanying drawings shall be interpreted as illustrative and not in a limiting sense.

The invention claimed is:

1. A method for dose planning for a radiation therapy system, the radiation therapy system comprising a radiation therapy unit, wherein a spatial dose distribution surrounding focus point can be changed by adjusting collimator settings of a collimator of said radiation therapy unit, said collimator having a plurality of collimator passage inlets directing radiation emanating from radioactive sources of a source carrier arrangement of the therapy system to the focus point, said method comprising:
   determining shots to be delivered during treatment, each shot being associated with an isocenter and being modelled by a spatial dose volume distribution of radiation, a shape of said spatial distribution depending on the specific collimator setting, including:
   a) selecting at least one isocenter position within a target;
   b) evaluating each isocenter based on predetermined conditions;
   c) selecting at least a specific collimator and sector setting for each isocenter based on the evaluation;
   d) calculating a dose for the selected isocenters;
   e) repeating the steps a)-d) until at least one stopping criteria has been reached, wherein a final set of isocenters are provided; and
   using the final set of isocenters in treatment planning.

2. The method according to claim 1, wherein steps a)-e) further comprises:
   b) evaluating a predetermined number of columns in a dose rate matrix for each isocenter based on the predetermined conditions, wherein each column include a specific collimator and sector setting;
   c) selecting at least one column for each isocenter based on the evaluation;
   d) calculating the dose for the selected isocenters;
   e) repeating the steps a)-d) until the at least one stopping criteria has been reached, wherein the final set of isocenters are provided; and
   using the final set of isocenters in treatment planning.

3. A method for dose planning for a radiation therapy system, the radiation therapy system comprising a radiation therapy unit, wherein a spatial dose distribution surrounding a focus point can be changed by adjusting collimator settings of a collimator of said radiation therapy unit, said collimator having a plurality of collimator passage inlets directing radiation emanating from radioactive sources of a source carrier arrangement of the therapy system to the focus point, wherein said collimator is arranged to be rotatable around an axis along a translational direction of a patient to allow radiation to be distributed in different angles to said focus point, said method comprising:
   determining shots to be delivered during treatment, each shot being associated with an isocenter and being modelled by a spatial dose volume distribution of radiation, a shape of said spatial distribution depending on the specific collimator setting, including:
   f) selecting isocenter positions within a target and/or angles in a predetermined angle range;
   g) evaluating each isocenter and/or angle based on predetermined conditions;
   h) selecting at least a specific collimator and sector setting for each isocenter and/or angle based on the evaluation;
   i) calculating a dose for the selected isocenters;
   j) repeating the steps f)-i) until at least one stop criteria has been reached, wherein a final set of isocenters and/or angles are provided; and
   using the final set of isocenters and/or angles in treatment planning.

4. The method according to claim 3, wherein steps f)-j) further comprises:
   g) evaluating a predetermined number of columns in a dose rate matrix for each isocenter and/or angle within a predetermined angle range based on the predetermined conditions, wherein each column include a specific collimator and sector setting;
   h) selecting at least one column for each isocenter and/or angle based on the evaluation;
   i) calculating the dose for the selected isocenters and/or angles;
   j) repeating the steps f)-i) until the at least one stop criteria has been reached, wherein the final set of isocenters and/or angles are provided; and
   using the final set of isocenters and/or angles in treatment planning.

5. The method according to claim 4, wherein the step of selecting includes keeping the columns for each angle and/or isocenter from the step selected in a prior iteration, removing columns for each angle and/or isocenter in the selected prior iteration, or removing a subset of columns for each angle and/or isocenter in the selected prior iteration based on the evaluation.

6. The method according to claim 3, wherein the step of evaluating comprises calculating a negative reduced cost using the cost function calculation:

$$r_m = c_m - \sum_{l=1}^{N_j} \lambda_l \phi_{lm},$$

where $c_m$ is the coefficient of an objective of the variable $x_1$, $\lambda_i$ are Lagrange multipliers and ($\phi_{im}$ is a dose rate kernel corresponding to the isocenter and the dose rate in a voxel j as a result of irradation with the DoF m, $N_j$ are the number of voxels and ($\phi_{im}$ is an element in the dose rate kernel.

7. The method according to claim 6, wherein the step of selecting comprises selecting at least one column for each angle and/or isocenter that results in the largest negative reduced cost in the cost function calculation.

8. The method according to claim 3, wherein said at least one stop criteria includes a predetermined number of isocenters, and/or a predetermined number of angles, and/or when a relative improvement is below a predetermined level of a cost function has been reached, and/or the isocenter having largest reduced cost below a limit $r_{stop}$ or the number of iterations, k, exceeds a predetermined limit, $n_m$.

9. A dose planning software for a radiation therapy system, the radiation therapy system comprising a radiation therapy unit having a fixed radiation focus point, wherein a spatial dose distribution surrounding the focus point can be changed by adjusting collimator settings of a collimator of said radiation therapy unit, said collimator having a plurality of collimator passage inlets directing radiation emanating from radioactive sources of a source carrier arrangement of the therapy system to said focus point, said dose planning software being configured to execute:
   determining shots to be delivered during treatment, each shot being associated with an isocenter and being modelled by a spatial dose volume distribution of radiation, a shape of said spatial distribution depending on the specific collimator setting, including:
   a) selecting at least one isocenter position within a target;
   b) evaluating each isocenter based on predetermined conditions;
   c) selecting at least a specific collimator and sector setting for each isocenter based on the evaluation;
   d) calculating a dose for the selected isocenters;
   e) repeating the steps a)-d) until at least one stopping criteria has been reached, wherein a final set of isocenters are provided; and using the final set of isocenters in treatment planning.

10. The dose planning software according to claim 9, wherein steps a)-e) further comprises:
   b) evaluating a predetermined number of columns in a dose for each isocenter based on the predetermined conditions, wherein each column include a specific collimator and sector setting;
   c) selecting at least one column for each isocenter based on the evaluation;
   d) calculating the dose including the selected isocenters;
   e) repeating the steps a)-d) until the at least one stopping criteria has been reached, wherein the final set of isocenters are provided; and
   using the final set of isocenters in treatment planning.

11. A dose planning software for a radiation therapy system, the radiation therapy system comprising a radiation therapy unit, wherein a spatial dose distribution surrounding a focus point can be changed by adjusting collimator settings of a collimator of said radiation therapy unit, said collimator having a plurality of collimator passage inlets directing radiation emanating from radioactive sources of a source carrier arrangement of the therapy system to the focus point, wherein said collimator is arranged to be rotatable around an axis along a translational direction of a patient to allow radiation to be distributed in different angles to said focus point, said dose planning software being configured to execute:
   determining shots to be delivered during treatment, each shot being associated with an isocenter and being modelled by a spatial dose volume distribution of radiation, a shape of said spatial distribution depending on the specific collimator setting, including:
   f) selecting isocenter positions within a target and/or angles in a predetermined angle range;
   g) evaluating each isocenter and/or angle based on predetermined conditions;
   h) selecting at least a specific collimator and sector setting for each isocenter and/or angle based on the evaluation;
   i) calculating a dose for the selected isocenters;
   j) repeating the steps f)-i) until at least one stopping criteria has been reached, wherein a final set of isocenters and/or angles are provided; and using the final set of isocenters and/or angles in treatment planning.

12. The dose planning software according to claim 11, wherein steps f)-j) further comprises:
   g) evaluating a predetermined number of columns in a dose for each isocenter and/or angle within the predetermined angle range based on the predetermined conditions, wherein each column include a specific collimator and sector setting;
   h) selecting at least one column for each isocenter and/or angle based on the evaluation;
   i) calculating the dose including the selected isocenters and/or angles;
   j) repeating the steps f)-i) until the at least one stopping criteria has been reached, wherein a final set of isocenters and/or angles are provided; and using the final set of isocenters and/or angles in treatment planning.

13. The dose planning software according to claim 12, wherein the step of selecting includes keeping the columns for each angle and/or isocenter from the step selected in a prior iteration, removing columns for each angle and/or isocenter in the selected prior iteration, or removing a subset of columns for each angle and/or isocenter in the selected prior iteration based on the evaluation.

14. The dose planning software according to claim 11, wherein the step of evaluating comprises calculating a negative reduced cost using the cost function calculation:

$$r_m = c_m - \sum_{l=1}^{N_j} \lambda_l \phi_{lm},$$

where $c_m$ is the coefficient of an objective of the variable $x_1$, $\lambda_i$ are Lagrange multipliers and $\phi_{im}$ is a dose rate kernel corresponding to the isocenter and the dose rate in a voxel j as a result of irradation with the DoF m, $N_j$ are the number of voxels and $\phi_{im}$ is an element in the dose rate kernel.

15. The dose planning software according to claim 14, wherein the step of selecting comprises selecting at least one column for each angle and/or isocenter that results in the largest negative reduced cost in the cost function calculation.

16. The dose planning software according to claim 11, wherein said at least one stopping criteria includes a predetermined number of isocenters, and/or a predetermined number of angles, and/or when a relative improvement is below a predetermined level of a cost function has been reached, and/or the isocenter having largest reduced cost below a limit $r_{stop}$ or the number of iterations, k, exceeds a predetermined limit, $n_{max}$.

17. A dose planning system for a radiation therapy system, the radiation therapy system comprising a radiation therapy unit having a fixed radiation focus point, wherein a spatial dose distribution surrounding the focus point can be changed by adjusting collimator settings of a collimator of said radiation therapy unit, said collimator having a plurality of collimator passage inlets directing radiation emanating from radioactive sources of a source carrier arrangement of the therapy system to said focus point, said dose planning system comprising a control console configured to:
  determine shots to be delivered during treatment, each shot being associated with an isocenter and being modelled by a spatial dose volume distribution of radiation, a shape of said spatial distribution depending on the specific collimator setting, including:
  a) select at least one isocenter position within a target;
  b) evaluate each isocenter based on predetermined conditions;
  c) select at least a specific collimator and sector setting for each isocenter based on the evaluation;
  d) calculate a dose for the selected isocenters;
  e) repeat the steps a)-d) until at least one stopping criteria has been reached, wherein a final set of isocenters are provided; and using the final set of isocenters in treatment planning.

18. The dose planning system according to claim 17, wherein steps a)-e) further comprises:
  b) evaluate a predetermined number of columns in a dose for each isocenter based on the predetermined conditions, wherein each column include a specific collimator and sector setting;
  c) select at least one column for each isocenter based on the evaluation;
  d) calculate the dose including the selected isocenters;
  e) repeat the steps a)-d) until the at least one stopping criteria has been reached, wherein a final set of isocenters are provided; and
  use the final set of isocenters in treatment planning.

19. A dose planning system for a radiation therapy system, the radiation therapy system comprising a radiation therapy unit, wherein a spatial dose distribution surrounding a focus point can be changed by adjusting collimator settings of a collimator of said radiation therapy unit, said collimator having a plurality of collimator passage inlets directing radiation emanating from radioactive sources of a source carrier arrangement of the therapy system to the focus point, wherein said collimator is arranged to be rotatable around an axis along a translational direction of a patient to allow radiation to be distributed in different angles to said focus point, said dose planning system comprising a control console configured to:
  determine shots to be delivered during treatment, each shot being associated with an isocenter and being modelled by a spatial dose volume distribution of radiation, a shape of said spatial distribution depending on the specific collimator setting, including:
  f) select isocenter positions within a target and/or angles in a predetermined angle range;
  g) evaluate each isocenter and/or angle based on predetermined conditions;
  h) select at least a specific collimator and sector setting for each isocenter and/or angle based on the evaluation;
  i) calculate a dose for the selected isocenters;
  j) repeat the steps f)-i) until at least one stopping criteria has been reached, wherein a final set of isocenters and/or angles are provided; and
  use the final set of isocenters and/or angles in treatment planning.

20. The dose planning system according to claim 19, wherein steps f)-j) further comprises:
  g) evaluate a predetermined number of columns in a dose for each isocenter and/or angle within a predetermined angle range based on the predetermined conditions, wherein each column include a specific collimator and sector setting;
  h) select at least one column for each isocenter and/or angle based on the evaluation;
  i) calculate the dose including the selected isocenters and/or angles;
  j) repeat the steps f)-i) until the at least one stopping criteria has been reached,
  wherein a final set of isocenters and/or angles are provided; and
  use the final set of isocenters and/or angles in treatment planning.

* * * * *